(12) United States Patent
Cournoyer et al.

(10) Patent No.: US 9,072,528 B2
(45) Date of Patent: Jul. 7, 2015

(54) INSTRUMENT AND METHOD TO ENHANCE ARTICULAR CARTILAGE REGENERATION

(71) Applicant: DePuy Mitek, LLC, Raynham, MA (US)

(72) Inventors: John R. Cournoyer, Norfolk, MA (US); Dina Belloli, Foxboro, MA (US); Jonathan Correia, Boston, MA (US); Scott Woodruff, Boston, MA (US); Bethany F. Grant, Scituate, MA (US); Joseph Hernandez, Sandwich, MA (US)

(73) Assignee: DePuy Mitek, LLC, Raynham, MA (US)

( * ) Notice: Subject to any disclaimer, the term of this patent is extended or adjusted under 35 U.S.C. 154(b) by 128 days.

(21) Appl. No.: 13/705,472

(22) Filed: Dec. 5, 2012

(65) Prior Publication Data

US 2014/0155896 A1    Jun. 5, 2014

(51) Int. Cl.
*A61B 17/16* (2006.01)
*A61B 17/32* (2006.01)
*A61B 17/34* (2006.01)

(52) U.S. Cl.
CPC ............ *A61B 17/16* (2013.01); *A61B 17/1617* (2013.01); *A61B 17/320016* (2013.01); *A61B 17/3472* (2013.01); *A61B 17/3478* (2013.01)

(58) Field of Classification Search
CPC . A61B 17/16; A61B 17/1617; A61B 17/3472
USPC .......................................... 606/79–85, 86 R
See application file for complete search history.

(56) References Cited

U.S. PATENT DOCUMENTS

| | | | | |
|---|---|---|---|---|
| 5,928,239 | A * | 7/1999 | Mirza .............................. | 606/79 |
| 6,425,887 | B1 * | 7/2002 | McGuckin et al. ............ | 604/272 |
| 6,932,834 | B2 * | 8/2005 | Lizardi et al. .................. | 606/232 |
| 8,409,230 | B2 * | 4/2013 | Pamichev et al. .............. | 606/167 |
| 2004/0147932 | A1 * | 7/2004 | Burkinshaw et al. ........... | 606/79 |
| 2005/0277971 | A1 * | 12/2005 | Melkent et al. ................ | 606/180 |
| 2011/0028977 | A1 | 2/2011 | Rauscher et al. | |
| 2011/0098709 | A1 * | 4/2011 | Malandain et al. ............. | 606/79 |

OTHER PUBLICATIONS

Kai Mithoefer et al., Chondral Resurfacing of Articular Cartilage Defects in the Knee with the Microfracture Technique, Surgical Technique, The Journal of Bone and Joint Surgery, Incorporated, pp. 294-304, 2006.
Kai Mithoefer et al., "Current Treatment Methods for Articular Cartilage Injury", Touch Briefing, pp. 108-112, 2009.
McGill et al., "Hip Microfracture: Indications, Technique, and Outcomes", Cartilage, 2010, pp. 127-136, 1(2).
Brian J. Cole, et al., "Surgical Management of Articular Cartilage Defects in the Knee", American Acadamy of Orthopaedic Surgeons, Selected Instructional Course Lectures, Jul. 2009, pp. 1777-1790, vol. 91-A, No. 7.

* cited by examiner

*Primary Examiner* — Christopher Beccia (57) ABSTRACT

A perforation instrument and method of using same, including a shaft capable of being inserted into a joint of a patient, having a longitudinal axis, and carrying at least one piercing member, each piercing member having a tip suitable to pierce sub-chondral bone. The instrument is capable of being altered between an exposed condition wherein the tip of the at least one piercing member is exposed and a safety condition wherein the tip of the at least one piercing member is not capable of piercing tissue.

6 Claims, 10 Drawing Sheets

INSTRUMENT AND METHOD TO ENHANCE ARTICULAR CARTILAGE REGENERATION

BACKGROUND OF THE INVENTION

1. Field of the Invention

The invention relates to devices for perforating sub-chondral bone within a joint of a patient.

2. Description of the Related Art

Cartilage on the articular surfaces of bones at joints within a body provide important protection for the underlying bone. The portions of bone supporting the articular cartilage are often referred to as sub-chondral bone. Both acute and chronic injury of articular cartilage causes chondral defects which can lead to progressive joint pain and impaired mobility.

Microfracture is an increasingly desired reparative procedure involving selective perforation of sub-chondral bone. There are a number of studies showing that microfracture beneath a chondral defect can result in a blood clot filling the chondral defect with pluripotent marrow-derived mesenchymal stem cells that produce beneficial fibrocartilage repair tissue.

Surgeons typically first debride unstable cartilage down to the sub-chondral bone layer to support subsequent basilar integration of the new repair tissue. Microfracture usually is accomplished thereafter using one or more rigid, curved awls that are manually manipulated through arthroscopic access sheaths or cannulas, and sometimes struck with a mallet, to create a series of microfracture holes in sub-chondral bone. Working space around chondral defects is usually limited and it is difficult to manipulate the awls effectively, especially within hip joints. A surgeon may need to exchange awls of different curvatures at different stages of the procedure. The cutting tips of the awls are exposed during insertion and withdrawal as well as during actual use on bone. Skiving of the awl tip across bone, often causing longitudinal disruptions and potential weakening of sub-chondral bone, and other unintended injury to bone and other tissue can occur.

It is therefore desirable to have a device insertable within a joint of a patient that easily enables multiple perforations of sub-chondral bone, even within a small working space.

SUMMARY OF THE INVENTION

An object of the present invention is to provide a low-profile instrument which facilitates multiple perforations of sub-chondral bone within a patient.

Another object of the present invention is to enable sufficient penetration of bone with less fatigue and more control for the surgeon or other user of the instrument.

A still further object of the present invention is to obviate the need to exchange instruments during a procedure.

Yet another object of the present invention is to provide an instrument which minimizes unintended damage to bone and other tissue, especially during insertion and withdrawal.

This invention features a perforation instrument including a shaft capable of being inserted into a joint of a patient, having a longitudinal axis, and carrying at least one piercing member, each piercing member having a tip suitable to pierce sub-chondral bone. The instrument further includes an actuation mechanism capable of altering the instrument between an exposed condition wherein the tip of the at least one piercing member is exposed and a safety condition wherein the tip of the at least one piercing member is not capable of piercing tissue.

In a number of embodiments, the actuation mechanism is capable of driving the tip of the at least one piercing member transverse to the longitudinal axis of the shaft and, in some embodiments, to extend the tip radially outwardly from the shaft. In certain embodiments, the at least one piercing member is curved along a plane substantially perpendicular to the longitudinal axis of the shaft. Preferably, the instrument includes a handle graspable by a hand of a user. In a number of embodiments, the shaft is generally cylindrical, sized to fit within a hip joint, has a working length of at least three centimeters, and has an outer diameter of less than ten millimeters.

In some embodiments, the actuation member includes a movable cover element that substantially encloses the at least one piercing member in the safety condition and is capable of being moved in a manner which exposes the at least one piercing member in the exposed condition. In one embodiment, the actuation member includes a plurality of articulated segments connected to the movable cover element.

This invention also features a method of performing microfracture of sub-chondral bone tissue, the method including selecting a region within a joint of a patient having sub-chondral bone to be perforated, and selecting a perforation instrument including a shaft having a longitudinal axis and carrying at least one piercing member, each piercing member having a tip suitable to pierce sub-chondral bone. The method further includes placing the instrument into a safety condition wherein the tip of the at least one piercing member is not capable of piercing tissue, and inserting the instrument, in the safety condition, into the joint of the patient in the vicinity of the selected region. The instrument is then altered into an exposed condition wherein the tip of the at least one piercing member is exposed, and multiple perforations are formed in the sub-chondral bone. The instrument is then returned to the safety condition and removed from the patient.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by a perforation instrument and method of using same, including a shaft capable of being inserted into a joint of a patient, having a longitudinal axis, and carrying at least one piercing member, each piercing member having a tip suitable to pierce sub-chondral bone. The terms "pierce", "perforate" and "perforation" refer to a pricking or puncture of bone tissue to form a hole. The instrument is capable of being altered between an exposed condition wherein the tip of the at least one piercing member is exposed and a safety condition wherein the tip of the at least one piercing member is not capable of piercing tissue.

Figure 1:
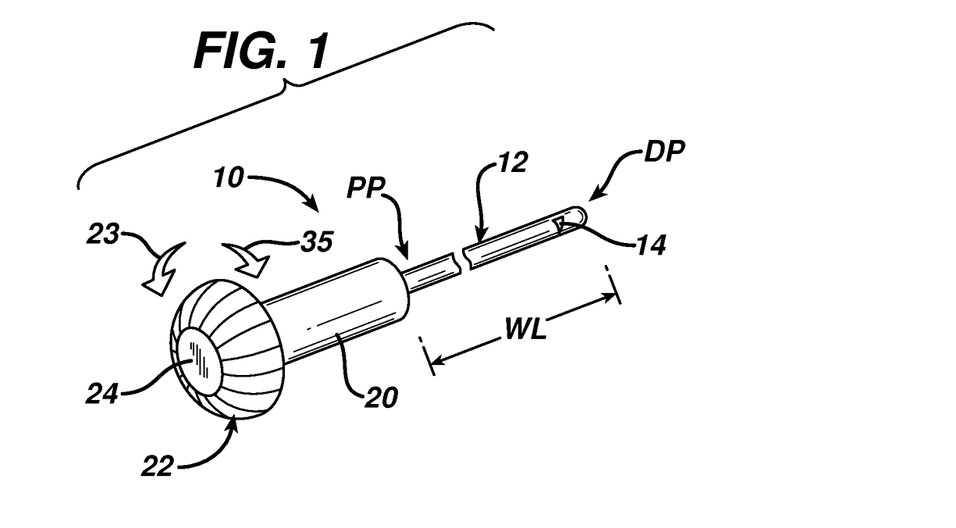
FIG. 1 is a schematic perspective view of a perforation instrument according to the present invention in a safety condition.
Figure 1A:
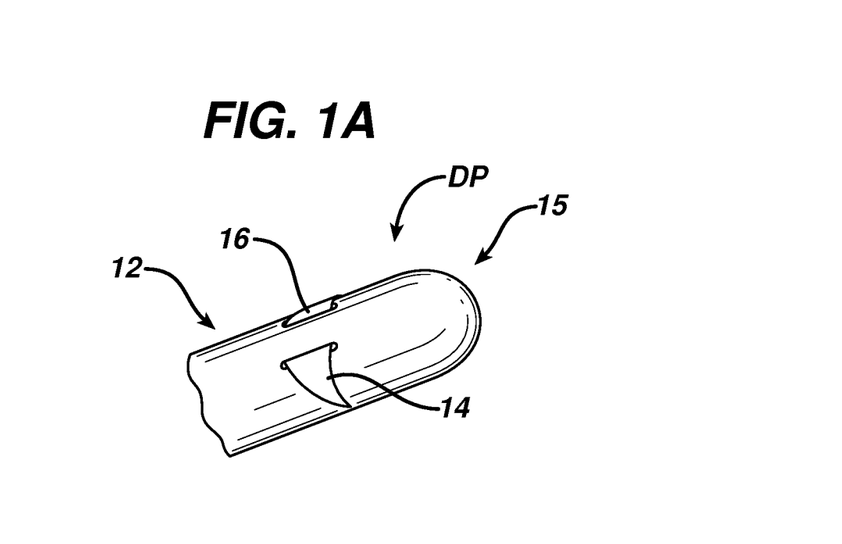
FIG. 1A is an enlargement of the distal portion DP of the instrument shown in FIG. 1.
Figure 2:
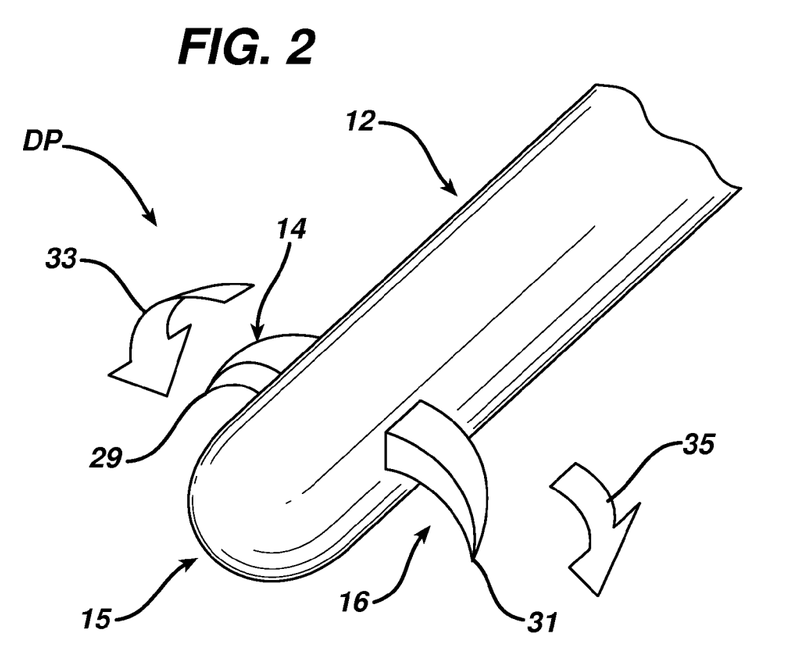
FIG. 2 is a schematic enlarged perspective view of the distal portion of the instrument of FIG. 1 in an exposed condition.
Figure 3:
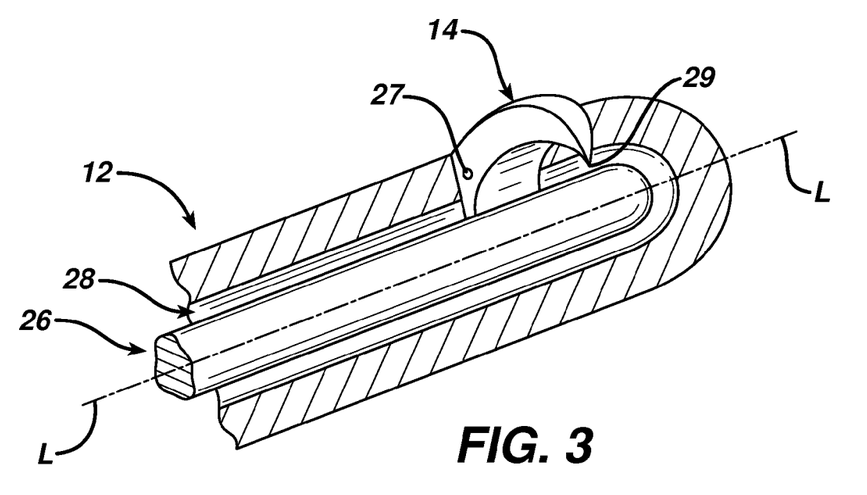
FIG. 3 is a schematic partial cross-sectional view of the distal portion of FIG. 2.
Figure 4A:
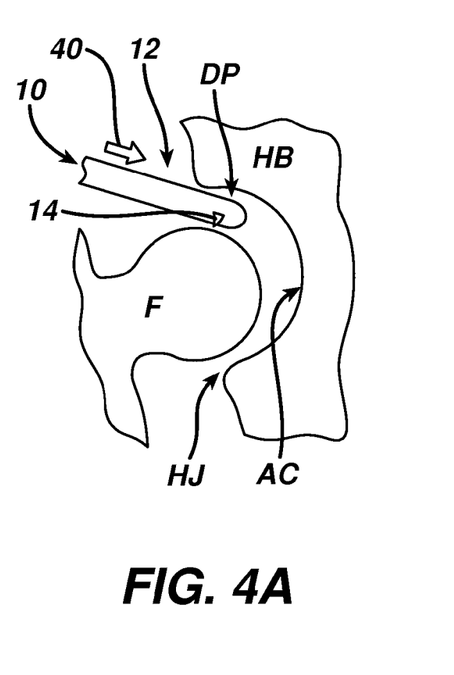
FIGS. 4A-4C are schematic illustrations of a microfracture procedure conducted according to the present invention in a hip joint.

An instrument 10 according to the present invention is illustrated in FIGS. 1, 1A and 4A in a first, safety condition and in FIGS. 2, 3, 4B and 4C in a second, exposed working condition as described in more detail below. A shaft 12 has a distal portion DP carrying at least one piercing member such as pivotable, radially extendable members 14 and 16 and having a rounded distal end 15.

A proximal portion PP, FIG. 1, of shaft 12 is connected to a handle 20 having an enlarged grip 22 in this construction. Handle 20 carries a button 24 which, when depressed, extends distally an inner cam member 26, FIG. 3, within lumen 28 of shaft 12. Distal extension of cam member 26 drives both piercing members 14 and 16 radially outwardly from the substantially flush positions shown in FIGS. 1 and 1A to the radially extended positions shown in FIGS. 2 and 3 to place instrument 10 in an exposed, working condition. In other constructions, one or more piercing members are controlled independently of other piercing members by separate cam members or other drive elements, such as described in more detail below. Piercing member 14 is pivotally connected to shaft 12 by a pin 27, FIG. 3, in this construction so that piercing tip 29 can be radially and arcuately extended, that is, tip 29 travels along a curve as it is deployed and retracted. It can further be appreciated that piercing member 14 itself is curved along a plane substantially perpendicular to the longitudinal axis L of the shaft 12.

Components of perforation instruments according to the present invention preferably are formed of biologically compatible, medical grade materials suitable for at least one type of conventional sterilization prior to surgical use. At least the piercing members preferably are formed of a biologically compatible metal or metal alloy such as medical grade stainless steel, for example SS 304 for single use, or of a harder grade material such as 17-4 hardened SS for reusable devices to maintain a sharp piercing tip. Other suitable materials include cobalt-chrome, titanium alloys, and certain ceramics. Portions of handle 20, such as grip 24, may have an enhanced gripping surface with a textured, higher-friction pattern that has been grit-blasted or etched; in other constructions a metallic, ceramic or polymeric material is attached by conventional processes to enhance manual gripping. The term "manual" also includes attachment and manipulation by a robotic arm. Arrows 23 and 25 represent counter-clockwise and clockwise rotational motion that can be imparted to handle 20 to generate motion in shaft distal portion DP, represented by arrows 35 and 33, FIG. 2, respectively, as described in more detail below.

Shaft 12 has a working length WL, FIG. 1, which can be inserted through a cannula or other access device as described in more detail below, or simply inserted percutaneously through soft tissue. In preferred constructions, working length WL is at least three centimeters in length and has an outer diameter of less than ten millimeters, more preferably less than or equal to approximately five millimeters. Working length WL is selected according to the orthopaedic procedure to be performed. For example, knee surgery or various types of shoulder surgery may require a working length WL of up to four to six inches (approximately 10-15 centimeters). Arthroscopic sheaths for knee surgery are typically at least three millimeters in diameter and three to five inches in length. Arthroscopic sheaths or cannulas for shoulder repair have the same or larger diameter, and are typically four to six inches in length. Arthroscopic sheaths or cannulas for hip repair typically have the same diameter range as for knee and shoulder procedures, but may be significantly longer, up to 18 cm or more in length.

During use of a perforation instrument according to the present invention to perform microfracture of sub-chondral bone tissue, a region within a joint of a patient is selected having sub-chondral bone to be perforated. A surgeon or other user selects a perforation instrument including a shaft having a longitudinal axis and carrying at least one piercing member, each piercing member having a tip suitable to pierce sub-chondral bone. The method further includes placing the instrument into a safety condition wherein the tip of the at least one piercing member is not capable of piercing tissue, and inserting the instrument, in the safety condition, into the joint of the patient in the vicinity of the selected region. The instrument is then altered into an exposed condition wherein the tip of the at least one piercing member is deployed or otherwise exposed within the joint, and multiple perforations are formed in the sub-chondral bone. The instrument is then returned to the safety condition and removed from the patient.

Figure 4B:
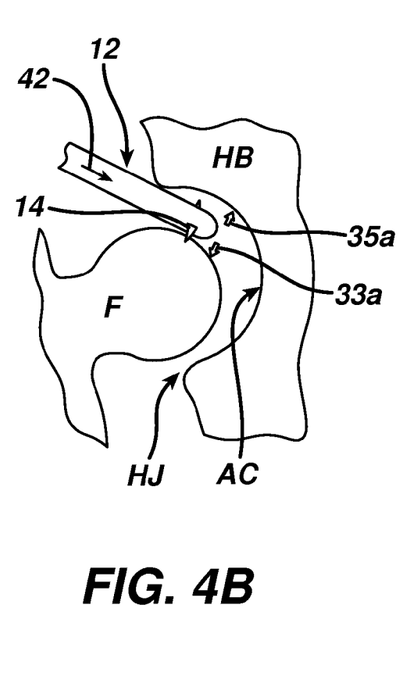
Figure 4C:
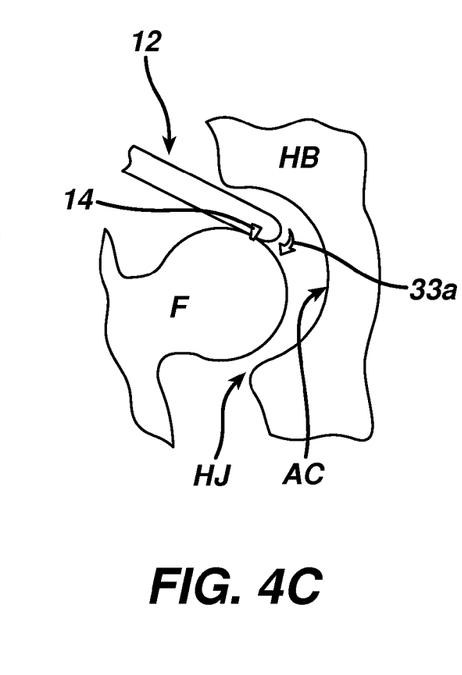

More specifically for the microfracture procedure illustrated in FIGS. 4A-4C utilizing instrument 10 described above, the distal portion DP of shaft 12, configured in the initial safety condition, is inserted distally, as indicated by arrow 40, FIG. 4A, into hip joint HJ between femur F and acetabulum AC of hipbone HB. Instrument 10 is altered into the exposed condition and further positioned as indicated by arrow 42, FIG. 4B, to bring piercing members 14 and 16 over the head region of femur F. Preferably, instrument 10 is rotated clockwise and counter-clockwise as depicted by arrows 33a and 35a, respectively, to impart a desired pattern of perforations in sub-chondral bone of femur F in this example. Piercing member 14 is shown puncturing femur F in FIG. 4C when shaft 12 is rotated in direction 33a. Sub-chondral bone on acetabulum AC or other regions within a joint can be treated in a similar manner.

The depth of holes formed by piercing according to the present invention preferably are sufficient to initiate blood flow including the release of fatty droplets. Actual depth varies according to patient and location, but generally are 2 mm to 3 mm deep, perhaps 4 mm or greater if there is a cartilage protrusion or raised area creating space between the top of the cartilage and the bone. If cartilage is not cut back to expose sub-chondral bone, even deeper tissue penetration may be required to access the marrow and initiate blood flow through the cartilage and into the sub-chondral bone.

The size of the damaged area to be perforated typically ranges between 1 cm to 2 cm. The density of holes is approximately 4 to 5 holes per square centimeter, with minimum spacing between holes of at least 2 mm, preferably 3 mm to 4 mm between holes so that sufficient bone bridges remain to provide structural support, that is, to preserve the integrity and function of the sub-chondral bone plate.

Figure 4D:
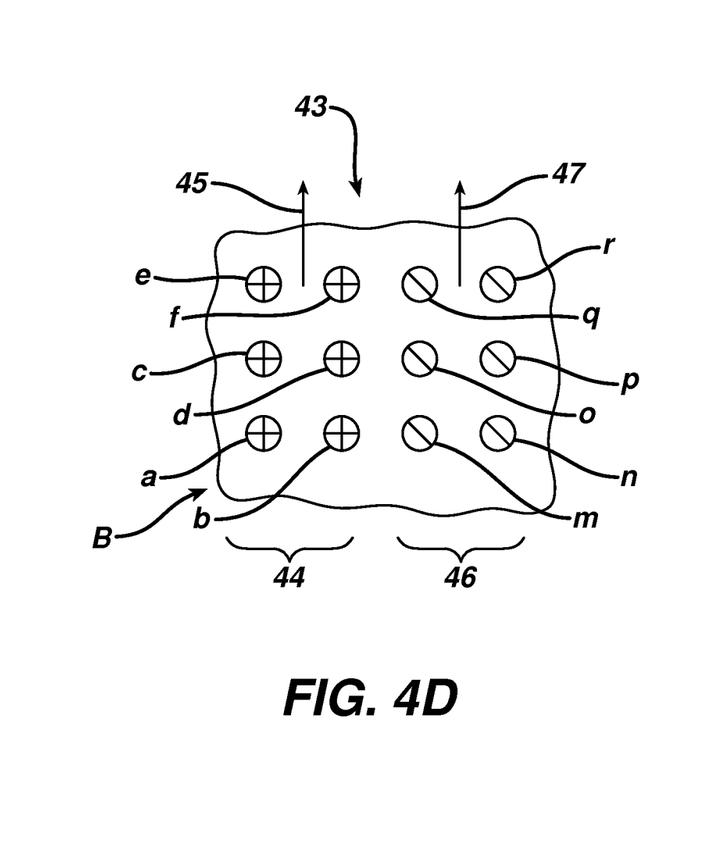
FIGS. 4D and 4E are schematic top views of different patterns of holes formed according to the present invention.

It will be appreciated by surgeons reading this disclosure that a dual pattern of holes can be easily generated by alternating, oscillating rotation of shaft 12 in the circumferential directions of arrows 33a and 35a while distal end 15 of shaft 12 is slowly advanced along the surface of sub-chondral bone. Grip 22 provides greater mechanical advantage over conventional awls, especially for transmitting rotational forces. One pattern 43 of holes generated according one method of the present invention is illustrated in FIG. 4D with a first set 44 of parallel holes a, b, c, d, e, and f, designated with "+" markings, and a second set 46 of parallel holes m, n, o, p, q, and r, designated with "\" markings for clarity. First set 44 is formed in one technique by deploying piercing members 14 and 16, FIGS. 2 and 3, and placing distal end 15, FIGS. 1A and 2, of instrument 10 in contact with sub-chondral bone B, FIG. 4D, such that piercing members 16 and 14 are positioned over the loci of holes a and b to be formed. Hole a is formed by rotating shaft 12 counter-clockwise until piercing member 16 punctures bone B to a desired depth. Shaft 12 is then rotated clockwise, without advancing distal end 15, until piercing member 14 punctures bone B to form hole b. Distal end 15 is then advanced one unit of length, typically 2 mm to 4 mm, in the direction of arrow 45, until piercing members 16 and 14 are positioned over the loci of holes c and d to be formed, respectively, and rotational force is successively applied in different directions without advancing distal end 15 until after both holes c and d are formed. After finishing with set 44, then distal end 15 is positioned to place piercing members 16 and 14 over the loci of holes m and n to complete set 46 in the direction of arrow 47.

Figure 4E:
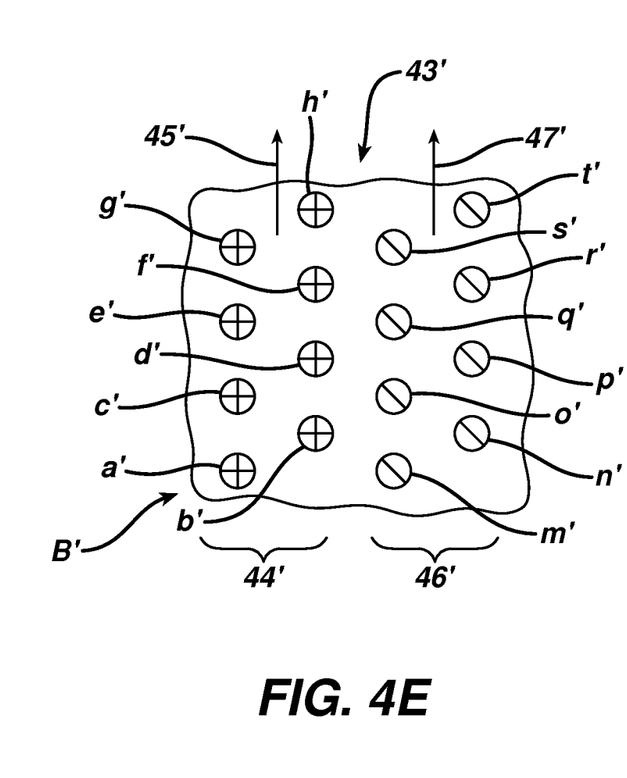

An alternative, second pattern 43' is shown schematically in FIG. 4E having a first set 44' of staggered holes a', b', c', d', e', f, g' and h', designated with "+" markings, and a second set 46' of staggered holes m', n', o', p', q', r', s' and t', designated with "\" markings for clarity. First set 44' is formed in one technique by deploying piercing members 14 and 16, FIGS. 2 and 3, and placing distal end 15, FIGS. 1A and 2, of instrument 10 in contact with sub-chondral bone B', FIG. 4E, such that piercing member 16 is positioned over the locus of hole a' to be formed. Hole a' is formed by rotating shaft 12 counter-clockwise until piercing member 16 punctures bone B' to a desired depth. Shaft 12 is advanced one-half a unit of length, in the direction of arrow 45', and then rotated clockwise until piercing member 14 punctures bone B' to form hole b'. Distal end 15 is then advanced one-half a unit of length, again in the direction of arrow 45', until piercing member 16 is positioned over the locus of hole c' to be formed. Rotational force is applied counter-clockwise to form hole c', and then distal end 15 is partially advanced and hole d' is formed by clockwise rotation of shaft 12. After finishing with set 44', then distal end 15 is positioned to place piercing member 16 over the locus of hole m' to complete set 46' in the direction of arrow 47'. A user can generate as many sets or partial sets as desired. In certain situations, it may be possible to generate a greater number of holes per unit area utilizing the second, staggered pattern, especially for ellipse-like or irregular areas.

Figure 5:
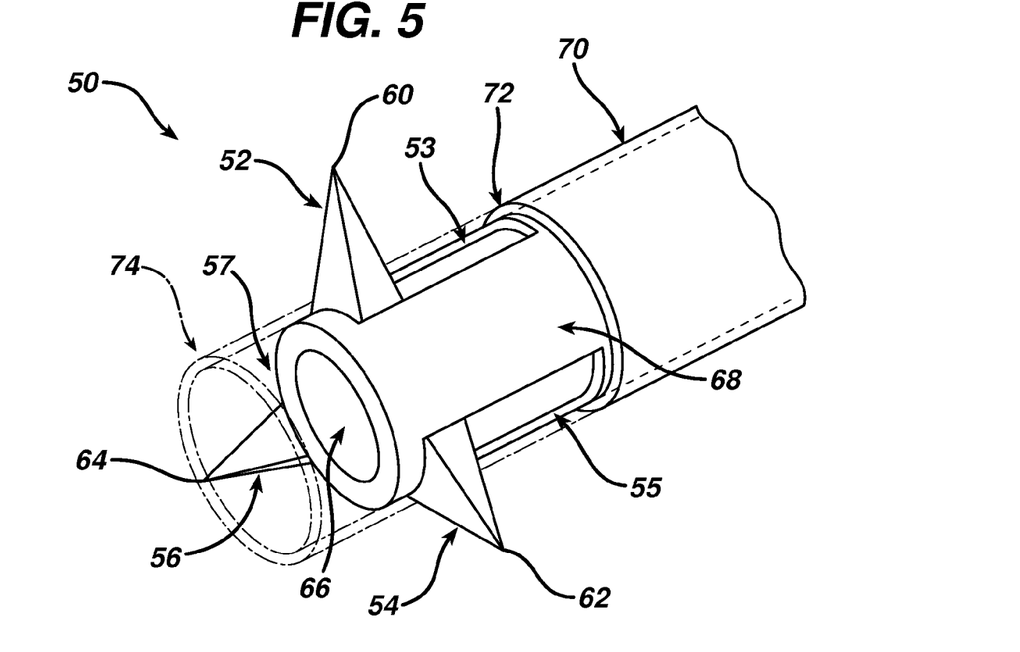
FIG. 5 is a schematic perspective view of the distal portion of an alternative instrument according to the present invention with an actuation member including a concentric outer sheath.

Other patterns of holes can be facilitated by providing additional piercing members and/or by altering their orientation or configuration, as well as by adjusting the successive movement of the instrument. For example, perforating instrument 50, FIG. 5, has three piercing members 52, 54 and 56 with triangular or pyramidal-type piercing tips 60, 62 and 64, respectively. The piercing members 52, 54 and 56 are biased outwardly through openings 53, 55 and 57 (not visible in FIG. 5) defined by shaft 68 when inner rod 66 is advanced distally as illustrated to achieve an extended condition. A safety condition is achieved by retracting rod 66 proximally and advancing outer concentric sleeve 70. A leading distal edge 72 of sleeve 70 assists driving piercing members 52, 54 and 56 radially inwardly as sleeve 70 is advanced distally, preferably to extend beyond shaft 68 as shown in phantom by dashed lines 74. In other constructions with a sufficient number of piercing members, a series of holes can be generated simply by rolling the distal portion over the sub-chondral bone, with the spacing of the piercing members establishing the spacing of the holes.

Figure 6:
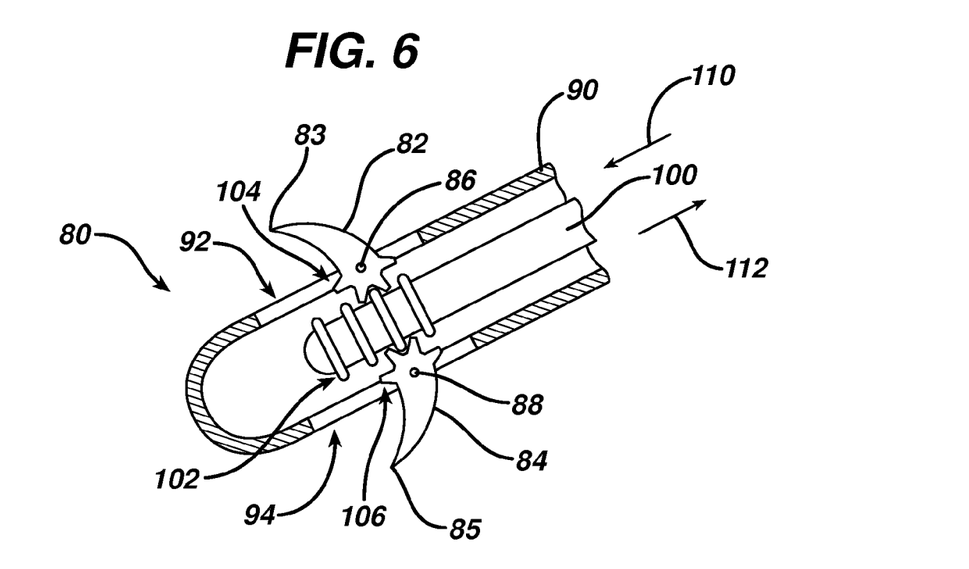
FIG. 6 is a schematic partial cross-sectional view of the distal portion of another instrument according to the present invention including rack-and-pinion-type elements.

Perforation instrument 80, FIG. 6, represents another construction according to the present invention. Piercing members 82 and 84, having penetration tips 83 and 85, are pivotally connected to shaft 90 by pins 86 and 88. Actuating rod 100 has a series of spaced projections or ribs 102 which engage teeth 104 and 106 of piercing members 82 and 84, respectively. Pushing rod 100 distally in the direction of arrow 110 or, when projections 102 are helical, rotating rod 100 so that it advances, drives piercing member 82 and 84 radially outwardly to the extended condition shown in FIG. 6. Conversely, pulling rod 100 proximally in the direction of arrow 112, or rotating rod 100 to retract it, then retracts members 82 and 84 within shaft 90 to a safety condition. The orientation of penetration tips 83 and 85 can thereby be altered as desired. In another construction, two half-round drive rods independently control the deployment and orientation of piercing members 82 and 84.

Figure 7:
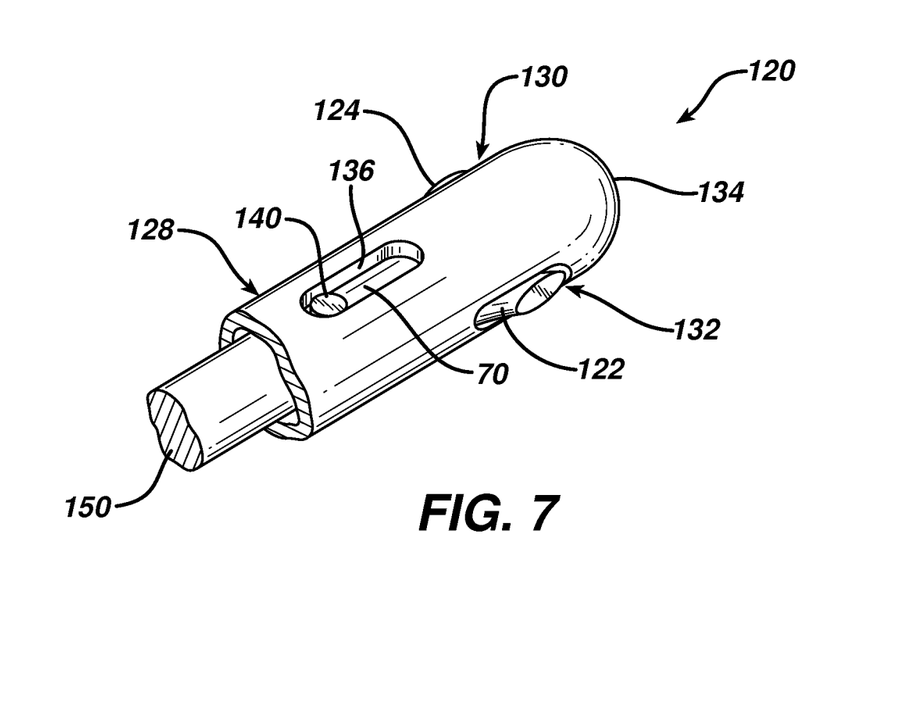
FIGS. 7-8 are schematic perspective views of the distal portion of yet another instrument according to the present invention in the safety and exposed conditions, respectively.
Figure 8:
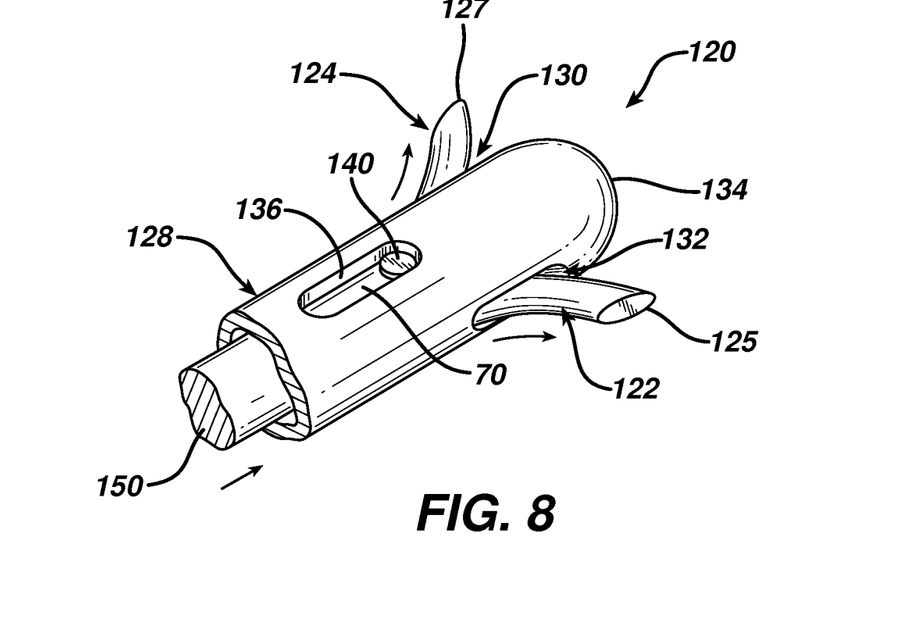

The distal portion of yet another perforation instrument 120 according to the present invention is shown in a safety condition in FIG. 7 and in an extended, working condition in FIG. 8. Piercing members 122 and 124, terminating in perforation tips 125 and 127, respectively, are extendable through openings 130 and 132 defined by shaft 128. Distal end 134 of shaft 128 is closed and rounded in this construction. A pin 140, visible through slot-shaped opening 136 in shaft 128 as shown in FIGS. 7 and 8, is carried by hole 161 in actuation rod 150 to pivotally capture piercing members 122, 124 via grooves 160, 162, FIGS. 9 and 10.

Figure 9:
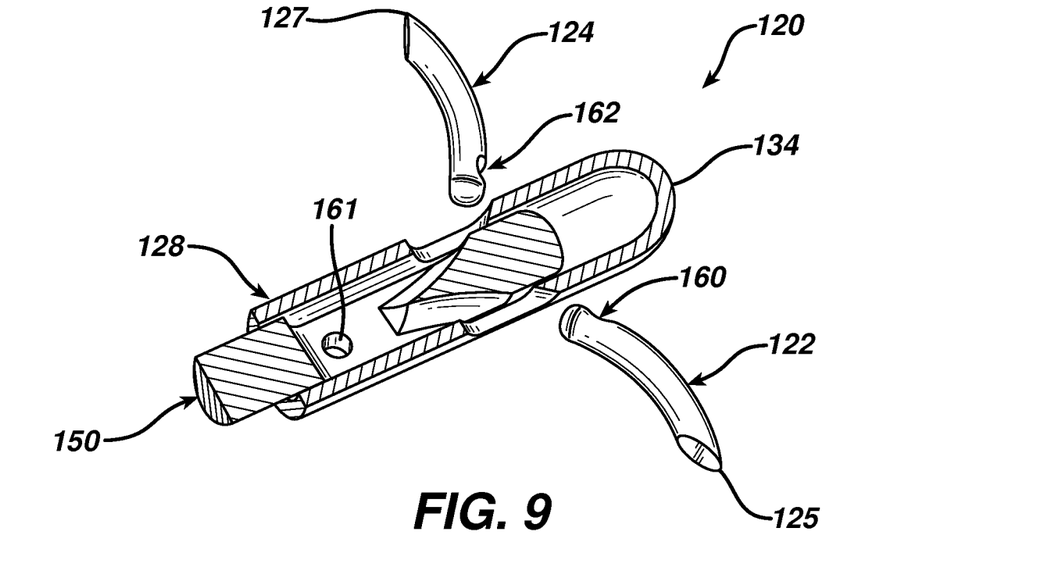
FIGS. 9 and 10 are partial cross-sectional views illustrating assembly of the instrument of FIGS. 7-8.
Figure 10:
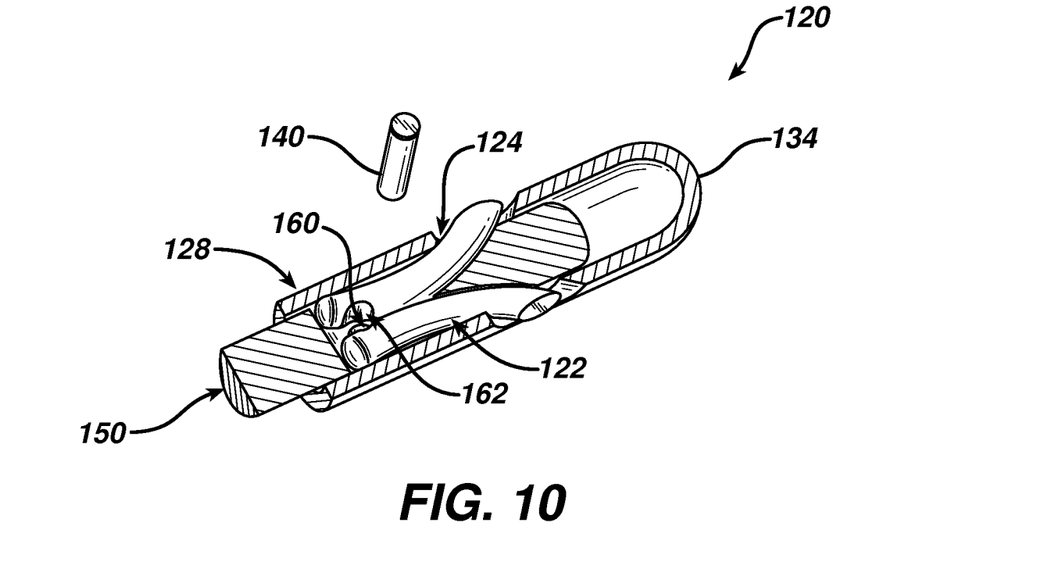

One construction of instrument 120 is based on modifications of suture anchor structure disclosed in U.S. Pat. No. 6,932,834 by Lizardi et al., which is incorporated herein by reference in its entirety. One technique for assembling the distal portion of instrument 120 is illustrated in FIGS. 9 and 10 herein.

Figure 11:
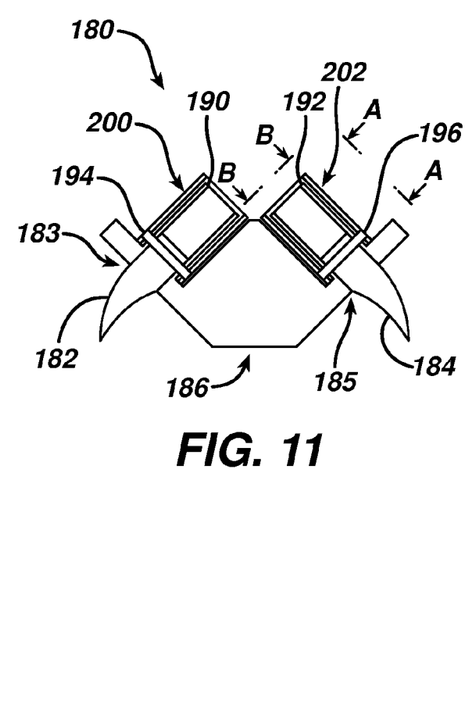
FIG. 11 is a schematic end view of another instrument according to the present invention having a yoke-and-slot-type elements.
Figure 12:
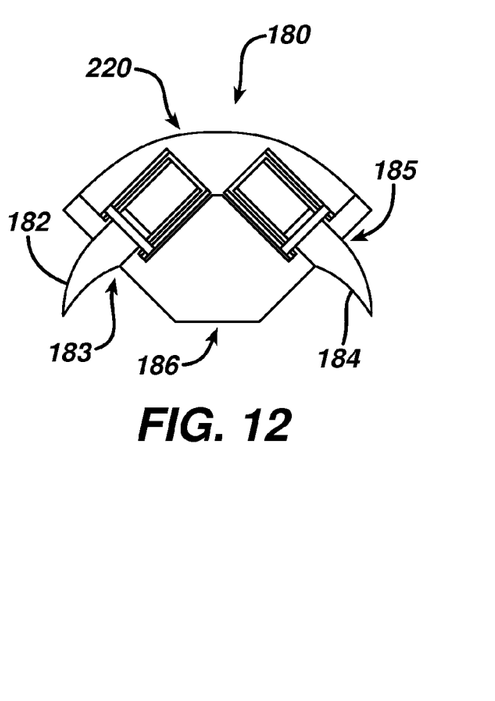
FIG. 12 is a schematic view similar to FIG. 11 with the addition of a cover element.

Perforation instrument 180 according to the present invention is shown in FIGS. 11-12 with piercing members 182 and 184 extended in an exposed, working condition through openings 183 and 185 defined by shaft 186. Piercing members 182 and 184 travel radially outwardly along a plane transverse to the longitudinal axis of shaft 186, that is, members 182 and 184 move in a linear radial path along the plane of the page containing FIGS. 11 and 12. Piercing members 182 and 184 are captured in passages defined by cylinders 190 and 192 by pins 194 and 196 which travel radially in slots defined by cylinders 190 and 192 and travel along an inclined path in slots defined in yokes 200 and 202.

Figure 11A:
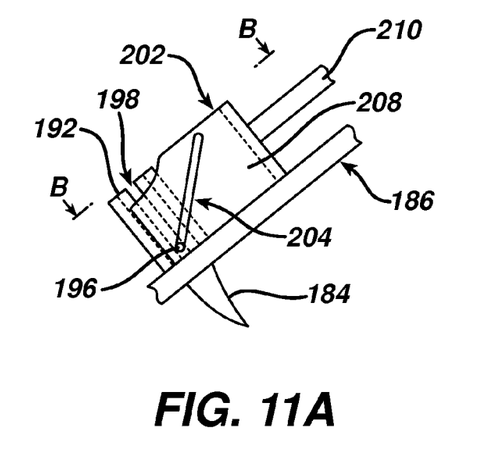
FIG. 11A is a partial schematic side view along lines A-A of FIG. 11.
Figure 11B:
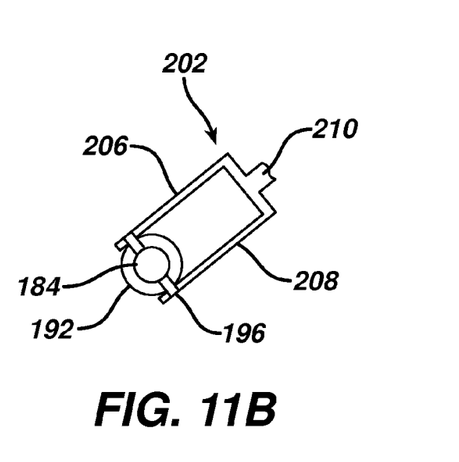
FIG. 11B is a top view along lines B-B of FIG. 11A.

FIG. 11A provides a side longitudinal view along lines A-A of FIG. 11 to show pin 196 within radial slot 198 defined by cylinder 192 and within inclined slot 204 defined by yoke 202. FIG. 11B provides a top view along lines B-B of FIG. 11A to show walls 206 and 208 of yoke 202. Distal force applied to actuation rod 210 drives yoke 202 distally to force pin 196 to move along yoke slot 204 and radially inwardly along cylinder slot 198.

Instrument 180 preferably includes a cover member 220, FIG. 12, to facilitate insertion and withdrawal of instrument 180 through an access device and relative to tissues. Cover member 220 is fixed in one construction, with cavities allowing travel by yokes 200 and 202.

Figure 13:
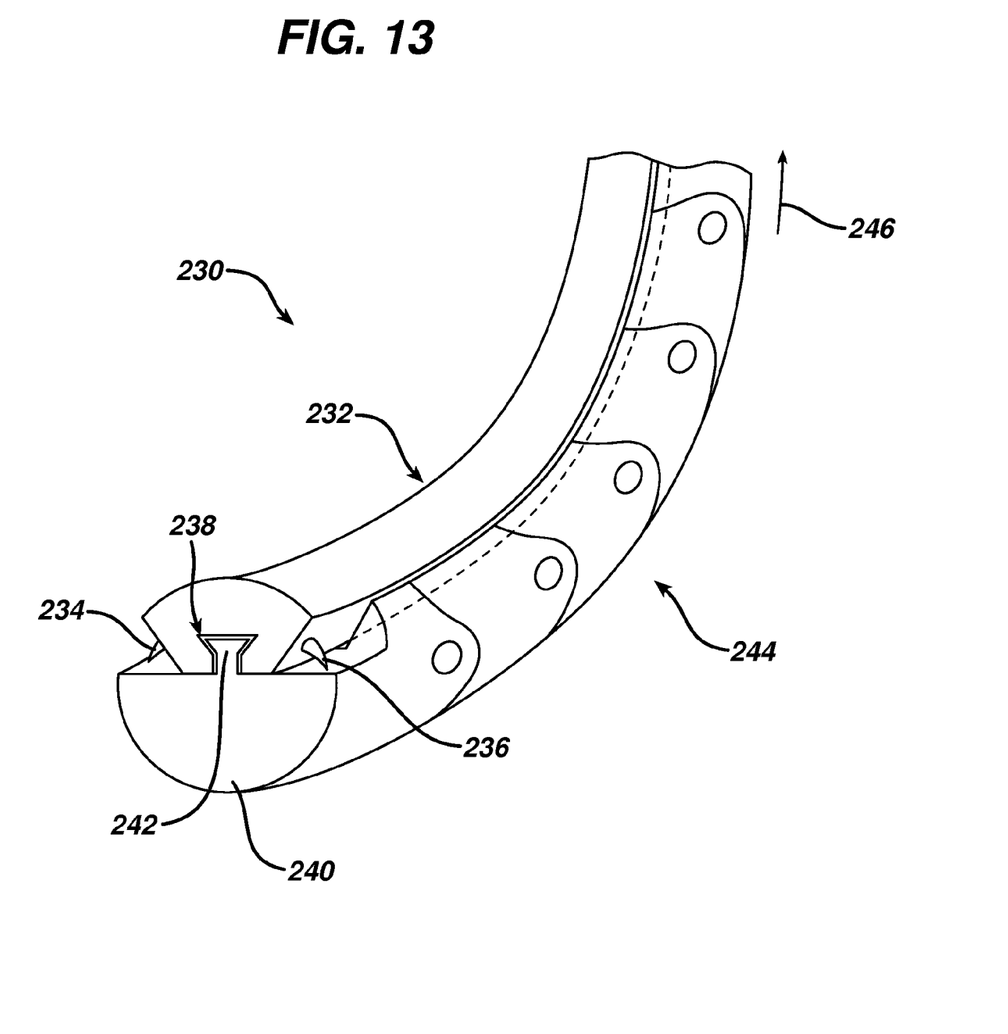
FIG. 13 is a schematic perspective view of the distal portion of a still further alternative instrument according to the present invention with an actuation member including articulating segments.

Although perforation instruments have been described above with movable piercing members, that is not a limitation of the invention. Instrument 230 according to the present invention is illustrated in FIG. 13 with curved shaft 232 carrying fixed piercing members 234 and 236 which are selectively exposed by a movable cover element 240. Shaft 232 defines a dovetail-type slot to slidably receive a corresponding projection 242 of cover element 240. A plurality of articulating segments 244 are slidably connected to shaft 232 in a similar manner. The articulations enable segments 242 to conform to the selected curvature of shaft 232. A proximal pulling force in the direction of arrow 246 applied to articulating segments 244 pulls cover element 240 proximally to expose piercing members 234 and 236. Conversely, a pushing force in a direction opposite to arrow 246 applied to articulating segments 244 will drive cover element 240 distally to shield piercing members 234 and 236 to return instrument 230 to a safety condition.

Figure 14:
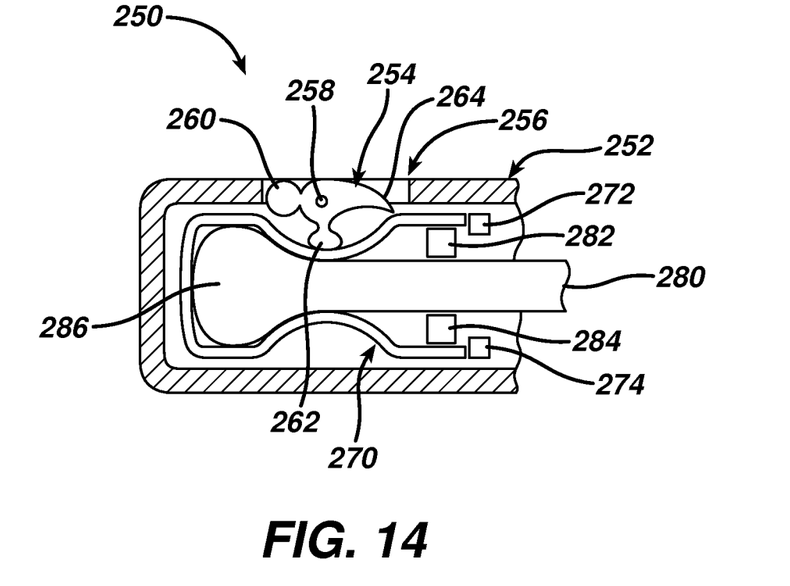
FIG. 14 is a schematic cross-sectional view of the distal portion of yet another alternative instrument according to the present invention with an actuation member including a plunger and a spring element.
Figure 15:
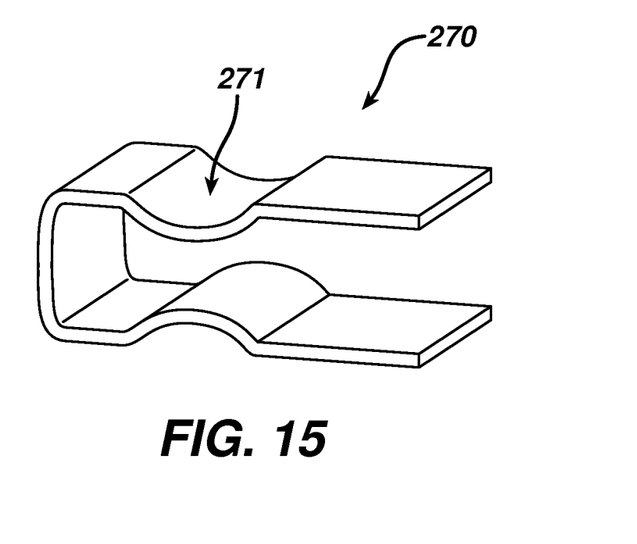
FIG. 15 is a schematic perspective view of the spring element of FIG. 14.

A perforation instrument 250 is shown in partial cross-section in FIG. 14 with shaft 252 defining a slot 256 and pivotally carrying a piercing member 254 pivotally connected by a pin 258. Piercing member 254 has a puncture tip 264 at one end and a first drive element 260 at an opposite end. A second drive element 262 is depicted contacting a narrowed portion 271 of a spring clip 270, which is illustrated in perspective view in FIG. 15. Spring clip 270 is captured within the lumen of shaft 252 by stops 272 and 274, FIG. 14. An actuating plunger rod 280 is held in part by guides 282 and 284. An enlarged head 286 at the distal end of rod 280 forces narrowed portion 271 radially outwardly to apply a rotational force on piercing member 254 via drive elements 260 and 262. For example, pulling rod 280 distally applies force to element 262 to drive tip 264 outwardly from a safety condition to an exposed condition.

Various mechanisms disposed on proximal portions of perforation instruments according to the present invention to be manipulated by a surgeon or other user to apply and transmit force to the distal portions of the instruments to deploy or retract piercing members will occur to those skilled in the art after reviewing this disclosure.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method of performing microfracture of sub-chondral bone tissue, comprising:
    selecting a region within a joint of a patient having sub-chondral bone to be perforated;
    selecting a perforation instrument including a shaft having a longitudinal axis and carrying at least one piercing member, each piercing member having a pointed tip suitable to pierce sub-chondral bone;
    placing the instrument into a safety condition wherein the tip of the at least one piercing member is not capable of piercing tissue;
    inserting the instrument, in the safety condition, into the joint of the patient in the vicinity of the selected region;
    altering the instrument into an exposed condition wherein the tip of the at least one piercing member is exposed;
    forming multiple perforations in the sub-chondral bone by rotating the shaft to contact the tip to the bone;
    returning the instrument to the safety condition; and
    removing the instrument from the patient.

2. The method of claim 1 wherein the shaft is rotated manually.

3. The method of claim 1 wherein the step of altering the instrument into the exposed condition comprises extending the piercing member radially outwardly from the shaft.

4. The method of claim 1 wherein the step of altering the instrument into the exposed condition comprises extending the piercing member transverse to the shaft.

5. The method of claim 1 wherein the step of altering the instrument into the exposed condition comprises extending the piercing member radially outwardly from the shaft, the piercing member being curved along a plane substantially perpendicular to the longitudinal axis of the shaft.

6. The method of claim 1 wherein the step of altering the instrument into the exposed condition comprises exposing two piercing members.

\* \* \* \* \*